(12) United States Patent
Lai et al.

(10) Patent No.: US 10,588,509 B2
(45) Date of Patent: *Mar. 17, 2020

(54) SEPARABLE MONITORING DEVICE AND METHOD

(71) Applicant: Medtronic Monitoring, Inc., San Jose, CA (US)

(72) Inventors: Arthur Lai, Minnetonka, MN (US); Jonathan Engel, Minneapolis, MN (US); Senthil Swaminathan, St. Paul, MN (US); Thomas Piaget, St. Paul, MN (US); Brett A. Landrum, Shoreview, MN (US); Scott Williams, Minneapolis, MN (US); Abhi Chavan, Maple Grove, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 15/851,093

(22) Filed: Dec. 21, 2017

(65) Prior Publication Data

US 2018/0132733 A1 May 17, 2018

Related U.S. Application Data

(62) Division of application No. 14/627,567, filed on Feb. 20, 2015, now Pat. No. 9,848,779.

(Continued)

(51) Int. Cl.
*A61B 5/00* (2006.01)
*A61B 5/0408* (2006.01)

(52) U.S. Cl.
CPC ........ *A61B 5/0006* (2013.01); *A61B 5/04085* (2013.01); *A61B 5/68335* (2017.08);

(Continued)

(58) Field of Classification Search
CPC .............. A61B 5/0006; A61B 5/04085; A61B 2560/0285
See application file for complete search history.

(56) References Cited

U.S. PATENT DOCUMENTS 4,216,462 A * 8/1980 McGrath ................. A61B 5/02
128/904
5,576,609 A * 11/1996 Brown ..................... H02J 7/008
320/164

(Continued)

FOREIGN PATENT DOCUMENTS

CN 101268932 A 9/2008
WO 2003009749 A1 2/2003

OTHER PUBLICATIONS

Extended European Search Report for Application No. 15751800.2, dated Aug. 25, 2018.

(Continued)

*Primary Examiner* — William J Levicky
(74) *Attorney, Agent, or Firm* — Shumaker & Sieffert, P.A.

(57) ABSTRACT

A patient monitoring device includes reusable and disposable portions. The disposable portion includes two or more electrodes for coupling to the skin of the patient, a battery, and a first set of electrical contacts. The reusable portion includes a processor, memory, a second set of electrical contacts, and sensing circuitry coupled to the at least two electrodes, wherein the reusable portion is mechanically coupleable to the disposable portion and wherein the reusable portion is electrically coupleable to the disposable portion through the first and second electrical contacts. The sensing circuitry and the processor are powered from the battery through the coupled first and second electrical contacts, and wherein when the reusable portion and the disposable portion are mechanically uncoupled after having (Continued)

been mechanically coupled, the disposable portion is rendered unusable by the process of mechanically uncoupling the reusable portion and the disposable portion.

13 Claims, 6 Drawing Sheets

Related U.S. Application Data

(60) Provisional application No. 61/948,973, filed on Mar. 6, 2014, provisional application No. 61/943,684, filed on Feb. 24, 2014.

(52) U.S. Cl.
CPC .......... *A61B 2560/0285* (2013.01); *A61B 2560/0443* (2013.01)

(56) References Cited

U.S. PATENT DOCUMENTS

| | | |
|---|---|---|
| 2006/0004719 A1 | 3/2006 | Jenkins |
| 2008/0139953 A1 | 6/2008 | Baker et al. |
| 2008/0234627 A1 | 9/2008 | Dent |
| 2008/0242962 A1 | 10/2008 | Roesicke et al. |
| 2009/0048529 A1 | 2/2009 | Chow |
| 2009/0076340 A1 | 3/2009 | Libbus et al. |
| 2009/0076344 A1 | 3/2009 | Libbus et al. |
| 2009/0076345 A1 | 3/2009 | Manicka et al. |
| 2010/0056896 A1 | 3/2010 | Park |
| 2011/0014470 A1 | 1/2011 | Yamamoto et al. |
| 2011/0152644 A1 | 6/2011 | Heck et al. |
| 2011/0245711 A1 | 10/2011 | Katra et al. |
| 2011/0319733 A1* | 12/2011 | Stafford .......... A61B 5/14532 600/345 |
| 2012/0010476 A1* | 1/2012 | Chambers .......... A61N 1/378 600/301 |
| 2012/0101396 A1 | 4/2012 | Solosko et al. |
| 2013/0116533 A1 | 5/2013 | Lian et al. |
| 2013/0317333 A1* | 11/2013 | Yang .................. A61B 5/00 600/372 |
| 2014/0066730 A1 | 3/2014 | Roesicke et al. |
| 2015/0087950 A1* | 3/2015 | Felix ................ A61B 5/0006 600/382 |
| 2018/0132733 A1 | 5/2018 | Lai et al. |

OTHER PUBLICATIONS

International Search Report Form PCT/ISA/210 for corresponding International Application No. PCT/US2015/016838 dated Jun. 10, 2015.

Written Opinion Form PCT/ISA/237 for corresponding International Application No. PCT/US2015/016838 dated Jun. 10, 2015.

* cited by examiner

UNBROKEN

BROKEN

US 10,588,509 B2

SEPARABLE MONITORING DEVICE AND METHOD

CROSS-REFERENCE TO RELATED APPLICATIONS

The present invention is a divisional of U.S. application Ser. No. 14/627,567 filed Feb. 20, 2015, which claims priority to U.S. Provisional Patent Application No. 61/943,684, titled "Physiological Monitoring Device and Method", filed Feb. 24, 2014 and U.S. Provisional Patent Application No. 61/948,973, titled "Separable Monitoring Device and Method", filed Mar. 6, 2014, both of which are incorporated by reference in their entirety. A claim of priority is made.

BACKGROUND OF THE INVENTION

Various devices have been developed for monitoring physiological parameters of a patient, for the detection, diagnosis, or prediction of health problems. For example, U.S. Patent Application Publications 2009/0076344 and 2009/0076345 describe adherent patches that monitor patient parameters such as tissue impedance, electrocardiogram signals, and other parameters, and transmit information wirelessly to a central server.

It is desirable that the cost of monitoring devices and services be kept low.

BRIEF SUMMARY OF THE INVENTION

In one aspect, a monitoring device for monitoring one or more physiological parameters of a patient comprises a disposable portion comprising at least two electrodes for coupling to the skin of the patient, a battery, and a first set of electrical contacts. The monitoring device further comprises a reusable portion comprising a processor, memory, a second set of electrical contacts, and sensing circuitry coupled to the at least two electrodes. The reusable portion is mechanically coupleable to the disposable portion and the reusable portion is electrically coupleable to the disposable portion through the first and second electrical contacts. When the reusable portion and the disposable portion are electrically coupled through the first and second electrical contacts, signals from the at least two electrodes are passed to the sensing circuitry and processed by the processor, the sensing circuitry and the processor are powered from the battery through the coupled first and second electrical contacts, and when the reusable portion and the disposable portion are mechanically uncoupled after having been mechanically coupled, the disposable portion is rendered unusable by the process of mechanically uncoupling the reusable portion and the disposable portion.

In another aspect, a monitoring device for monitoring one or more physiological parameters of a patient includes a disposable portion and a reusable portion. The disposable portion comprises at least two electrodes for coupling to the skin of the patient, a battery, and a first set of electrical contacts. The reusable portion comprises a processor, memory, a second set of electrical contacts, and sensing circuitry coupled to the at least two electrodes, wherein the reusable portion is mechanically coupleable to the disposable portion such that when the reusable portion and the disposable portion are mechanically coupled they form a water-resistant unit, and wherein the reusable portion is electrically coupleable to the disposable portion through the first and second electrical contacts. In addition, when the reusable portion and the disposable portion are electrically coupled through the first and second electrical contacts, signals from the at least two electrodes are passed to the sensing circuitry and processed by the processor, and wherein the sensing circuitry and the processor are powered from the battery through the coupled first and second electrical contacts. In addition, the reusable portion and the disposable portion are separable, and wherein the reusable portion can be used with a different disposable portion.

A monitoring device for monitoring an electrocardiogram of the patient includes a disposable portion and a reusable portion. The disposable portion includes a shell having a bay and a first surface for adhering to the skin of a patient. The disposable portion includes at least two skin electrodes on the first surface of the shell, a battery housed within the shell, and a first set of electrical contacts within the bay and in electrical communication with the battery and the skin electrodes. The reusable portion is releasably received and mechanically coupled within the bay of the disposable portion. The reusable portion comprises a monitoring circuit and a second set of electrical contacts in electrical communication with the monitoring circuit. The bay of the disposable portion and the reusable portion include interlocking features that releasably lock the reusable portion in the bay of the disposable portion with the second set of electrical contacts in electrical contact with the first set of electrical contacts such that the skin electrodes and battery of the disposable portion are in electrical communication with the monitoring circuit of the reusable portion. The bay includes first and second ends, the first set of electrical contacts being arranged along the first end, the interlocking features including a breakable feature arranged along the second end.

DETAILED DESCRIPTION OF THE INVENTION

Figure 1A:
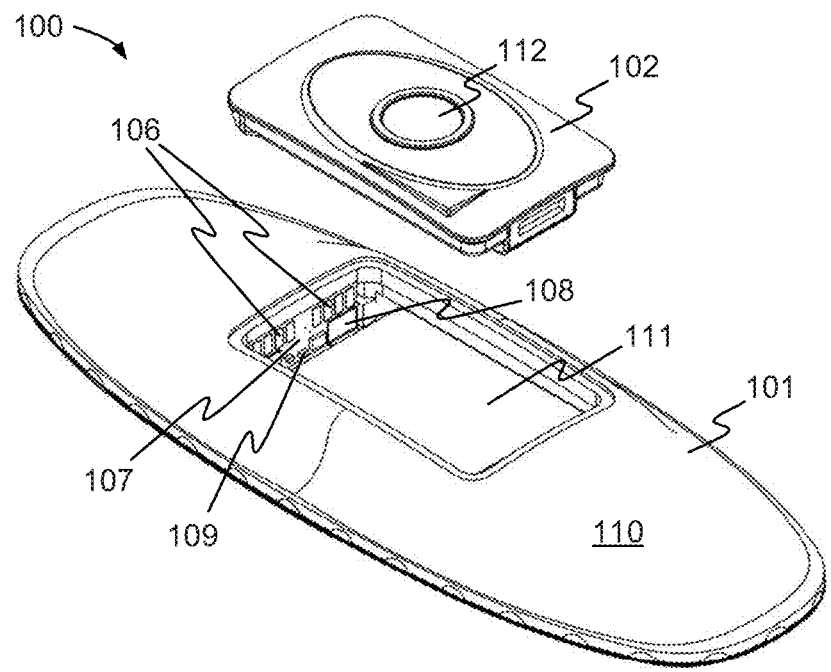
FIG. 1A illustrates an exploded view of a monitoring device in accordance with embodiments of the invention.

FIG. 1A illustrates an exploded view of a monitoring device 100 in accordance with embodiments of the invention. Monitoring device 100 is capable of monitoring one or more physiological parameters of a patient. Device 100 includes a disposable portion 101 and a reusable portion 102.

Figure 1B:
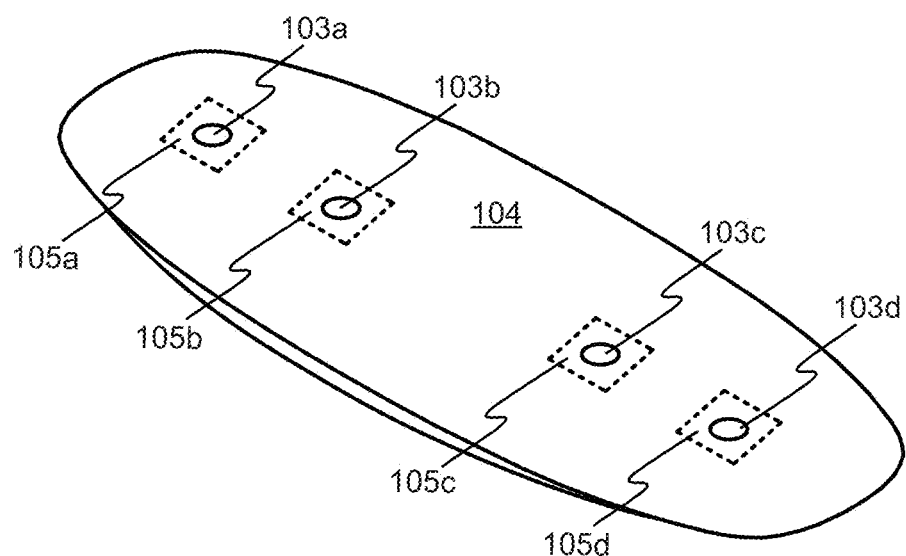
FIG. 1B shows a reverse angle view of a disposable portion of the monitoring device of FIG. 1A.

FIG. 1B shows a reverse angle view of disposable portion 101. Disposable portion 101 includes a number of electrodes 103a-103d. While four electrodes are shown in this example, different numbers of electrodes may be provided, depending on the physiological parameter or parameters a particular device is intended to monitor. Electrodes 103a-103d are configured to couple to the skin of the patient. For example, device 100 may be adhered to the thorax of the patient using an adhesive layer on the bottom side of bottom layer 104. Device 100 may be initially supplied with a release layer (not shown) that protects the adhesive and electrodes during shipping and storage, and that is removed before adhering the device to the patient. In some embodiments, electrodes 103a-103d are overlaid by a gels held in pockets 105a-105d formed between bottom layer 104 and another internal layer. The gels may enhance electrical contact between electrodes 103a-103d and the patient's skin. Additional details of possible arrangements of electrodes, gels, and structural layers usable in embodiments of the invention may be found in US Patent Application Publication 2011/0144470 published Jun. 16, 2011 and titled "Body Adherent Patch with Electronics for Physiologic Monitoring", the entire disclosure of which is incorporated by reference herein for all purposes.

Each of electrodes 103a-103d is electrically connected to one of a first set of electrical contacts 106. For example, electrodes 103a-103d may be formed on a flexible circuit that includes electrical traces that connect electrodes 103a-103d to electrical contacts 106. Electrical contacts 106 may be formed on a printed circuit board 107 that also includes a connector 108 for receiving a flex circuit or other connection to electrodes 103a-103d. Some electronic components 109 may also be provided on printed circuit board 107. Disposable portion 101 also includes a battery (not visible in FIGS. 1A and 1B).

The outer portion of disposable portion 101 may be covered with a flexible, breathable material 110 that is waterproof or water resistant, and is sealed around the edges directly or indirectly to bottom layer 104, so that device 100 can withstand being splashed with water without compromising the usability of the device. For example, material 110 may be a cloth including polyester, polyamide, nylon, and/or elastane (Spandex™). The breathable fabric may be coated or otherwise configured to make it water resistant or waterproof. In other embodiments, the outer portion of disposable portion 101 may be made of a non-breathable material, and moisture egress from the patient's skin may be provided by openings within the material.

Reusable portion 102 contains electronic components as described in more detail below. Reusable portion 102 includes a second set of electrical contacts (not visible in FIGS. 1A and 1B) that are complementary to first electrical contacts 106, so that signals from electrodes 103a-103d are coupled to reusable portion 102 when the two sets of contacts are engaged. Power from the battery in disposable portion 101 is also transferred through electrical contacts 106, to power reusable portion 102.

In this example, reusable portion 102 snaps securely into a frame formed around pocket (or bay) 111. Preferably, reusable portion 102 is a sealed module that can also withstand being splashed with water. Preferably, when disposable portion 101 and reusable portion 102 are mechanically coupled together, they form a water resistant unit. For example, reusable portion 102 may fit snugly enough into pocket 111 to substantially prevent the ingress of splashed water into pocket 111, or may be sealed using a gasket or the like. Preferably, the adhesive on bottom side 104 is also water resistant and has a high moisture vapor transmission rate, so that device 100 can be worn for extended periods while allowing the user to participate in normal daily activities, including showering. For example, in some embodiments, bottom layer 104 may be made of MED 5021 polyurethane film available from Avery Dennison Corporation of Pasadena, Calif., USA, or Tegaderm™ film available from the 3M Company of St. Paul Minn., USA, or a similar material. The material of bottom layer 104 may have a moisture vapor transmission rate of at least 100 g/m²/24 hrs, at least 400 g/m²/24 hrs, or another suitable value. In some embodiments, device 100 can be worn for up to 180 hours or more without being removed from the patient.

Button 112 may be actuated by the patient as is explained in more detail below.

Figure 2A:
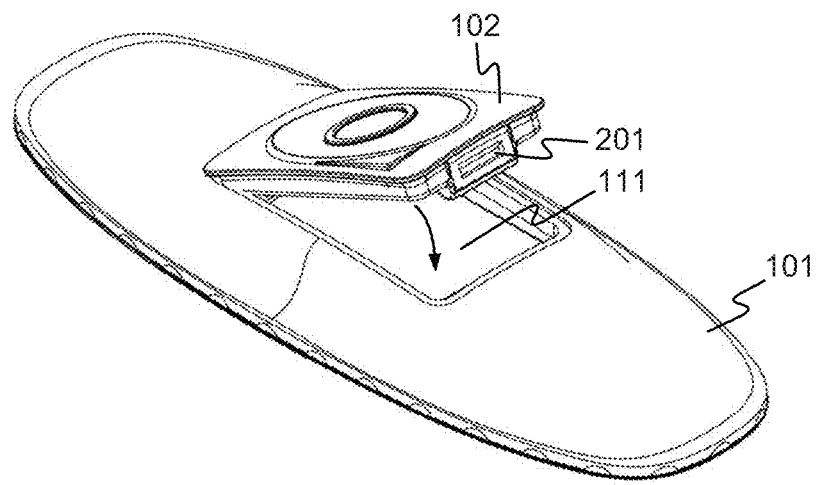
FIGS. 2A and 2B illustrate the process of mechanically coupling a reusable portion and a disposable portion of the monitoring device of FIGS. 1A and 1B.
Figure 2B:
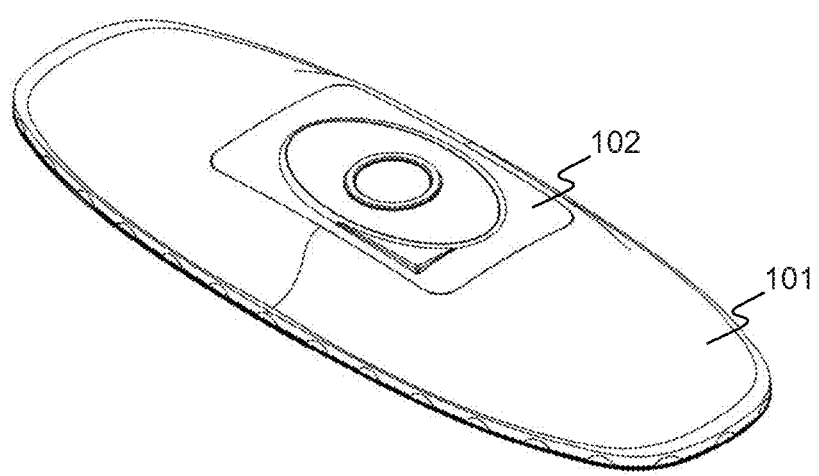

FIGS. 2A and 2B illustrate the process of mechanically coupling reusable portion 102 with disposable portion 101. In FIG. 2A, reusable portion 102 has been positioned to hook the far edge of reusable portion 102 (not visible in FIG. 2A) with the far edge of pocket 111. A snap feature 201 is configured to engage with a complementary feature (not visible) on the near edge of pocket 111. Reusable portion 102 is then rotated downward to engage snap feature 201, so that device 100 is assembled into the configuration shown in FIG. 2B. Preferably, device 100 is not disassemblable by the user to separate reusable portion 102 from disposable portion 101.

Figure 3:
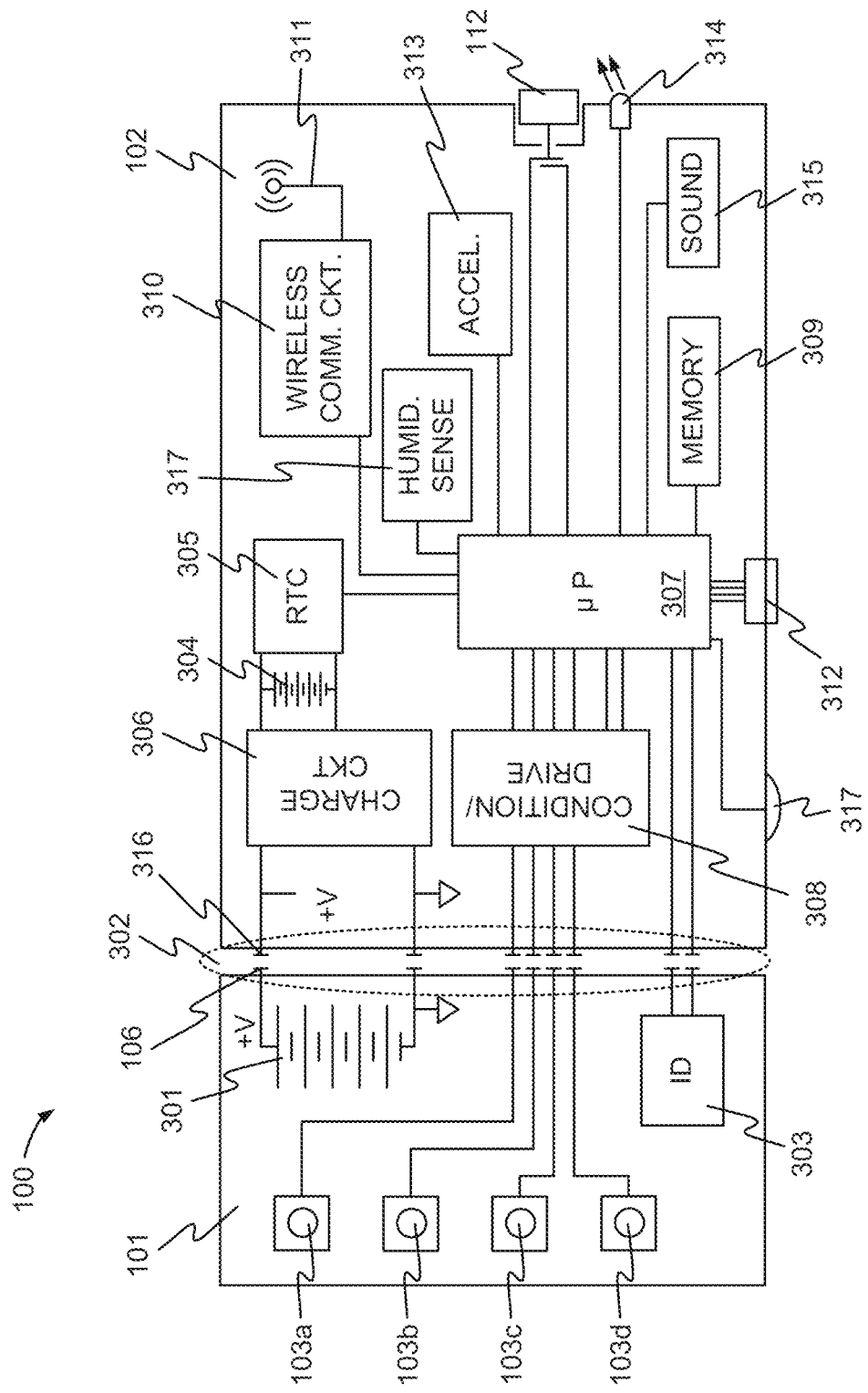
FIG. 3 illustrates a conceptual schematic view of an electronic architecture of the monitoring device of FIGS. 1A and 1B, in accordance with embodiments of the invention.

FIG. 3 illustrates a conceptual schematic view of an electronic architecture of monitoring device 100, in accordance with embodiments of the invention. Disposable portion 101 includes electrodes 103a-103d, and a primary battery 301. Primary battery 301 preferably has sufficient energy storage capacity to power monitoring device 100, including reusable portion 102, for a complete monitoring period, for example up to 180 hours or more. Electrodes 103a-103d and the terminals of battery 301 are connected through electrical contacts 302 to reusable portion 102. Electrical contacts 302 include first electrical contacts 106 on disposable portion 101, as well as second electrical contacts 316 on reusable portion 102. Electrical contacts 302 are engaged when disposable portion 101 and reusable portion 102 are assembled to each other.

Disposable portion 101 also includes a disposable portion identifier 303, which is also communicated to reusable portion 102 through electrical contacts 302. The depiction of disposable portion identifier 303 and its connection to reusable portion 102 in FIG. 3 is conceptual, and this functionality may be implemented using any suitable technique or combination of techniques. For example, disposable portion identifier may be stored in a memory addressable through electrical contacts 302, may be configured using a set of switches or fusible links that can be sensed through electrical contacts 302, may be repeatedly serially transmitted on a signal line, or may be implemented in some other way. The storage and transmission of disposable portion identifier 303 may be passive (not requiring any power) or may require electrical power, in which case power is supplied from primary battery 301, from the signal lines of processor 307 described below, or from another source. Power distribution lines are not depicted in FIG. 3 so as not to obscure the operation of the device in unnecessary detail. Similarly, certain connections between components are simplified. For example, certain connections that involve multiple signal paths or a combination of power and signal paths may be shown using a single line. In other cases, amplification or buffering circuitry and the like may not be shown.

Reusable portion 102 comprises a secondary battery 304 and a real time clock 305 powered by secondary battery 304. Secondary battery 304 may be, for example, a rechargeable lithium ion battery or another suitable kind of battery. Real time clock 305 enables reusable portion 102 to maintain an accurate time, even when reusable portion 102 is not connected to any disposable portion 101, and does not receive power from primary battery 301. Because secondary battery 304 need only power real time clock 305, it may have a smaller energy storage capacity than primary battery 301. Reusable portion 102 also comprises charging circuit 306, for charging secondary battery 304 using energy from primary battery 301, when available.

In other embodiments, a single battery may be used, residing in reusable portion 102. The single battery may have enough capacity to power monitoring device 100 for up to 180 hours or more, and may be rechargeable through electrical contacts such as contacts 316 on reusable portion 102. The single battery may also be able to power real time clock 305 for longer periods. Any necessary power for components in disposable portion 101 may be transferred through the contacts. The single battery may be recharged at any suitable time, for example before reusable portion 102 is installed in a new disposable portion 101, or when data is read from reusable portion 102 at the end of a monitoring period as is described in more detail below. In other embodiments, the single battery may be replaceable, and may be replaced each time reusable portion 102 is assembled into a new disposable portion 101. The replaced battery may preferably be rechargeable off line.

Referring again to FIG. 3, reusable portion 102 also includes a processor 307 for controlling the operation of monitoring device 100, analyzing signals, and communicating with other devices. Processor 307 may be, for example, a microprocessor as depicted in FIG. 3, or may be a microcontroller, digital signal processor, programmed gate array, or another kind of circuitry that can perform the necessary functions.

Signals from electrodes 103a-103d are coupled to processor 307 through contacts 302. The coupling may be direct, or additional circuitry may be present between electrodes 103a-103d and processor 307, for example signal conditioning circuitry, drive circuitry, switching circuitry, and the like. In FIG. 3, such circuitry is depicted as conditioning/drive circuitry 308. Conditioning/drive circuitry 308 may include, for example, signal conditioning amplifiers, noise filters, or the like.

In some embodiments, individual ones of electrodes 103a-103d may perform different functions at different times. For example, at one time, processor 307 may configure monitoring device 100 to measure an electrocardiogram (ECG) of the patient using two or three of the electrodes, and at another time, processor 307 may configure monitoring device 100 to measure a tissue impedance of the patient by driving a known alternating current between electrodes 103b and 103c, and measuring the voltage impressed between electrodes 103a and 103d. In order that electrodes 103a-103d can perform multiple functions, switching circuitry may be provided that switches electrodes between driving and sensing modes, for example. Additional details of such switching circuitry may be found in U.S. Patent Application Publication No. 2009/0076345 published Mar. 19, 2009 and titled "Adherent Device with Multiple Physiological Sensors", the entire disclosure of which is incorporated by reference herein for all purposes.

Reusable portion 102 further includes memory 309 accessible by processor 307. While only a single block is shown in FIG. 3, it will be understood that memory 309 may comprise one or more kinds of memory, including one or more of random access memory (RAM), read only memory (ROM), flash memory, electrically erasable programmable read only memory (EEPROM), or other kinds of memory. Memory 309 may hold instructions for processor 307, such that the functions of monitoring device 100 are caused to be carried out when processor 307 executes the instructions. Memory 309 preferably also stores a unique reusable portion identifier. In addition, data monitored from electrodes 103a-103d may be stored in memory 309, as is described in more detail below.

Reusable portion 102 further includes wireless communication circuitry 310 and an antenna 311, for wirelessly transmitting and receiving information to and from one or more external devices. For example, wireless communication circuitry 310 may implement a protocol such as Bluetooth®, ZigBee®, Wi-Fi®, or another kind of standard or proprietary protocol.

Button 112 enables a user of monitoring device 100 to signal processor 307. A connector 312 may be provided for communicating with an external device via a cable or other wired connection. Connector 312 may be, for example, part of a Universal Serial Bus (USB) interface, or another kind of standard or proprietary interface. In some embodiments, an accelerometer 313 enables measurement of the patient's orientation and activity level.

One or more light sources 314 may be provided for indicating the state of monitoring device 100 or for communicating other information. For example, light source 314 may be a light emitting diode that is under control of processor 307. Light source 314 may produce light of a single color, or may be multi-colored. Information may be communicated using light source 314 by using a particular color, flashing pattern, or both. For example, normal operation may be indicated by a periodic flash of green light from light source 314, and an error condition may be indicated by emitting steady red light. Many other techniques are possible for communicating information. In some embodiments, more than one light source 314 may be provided, and information may be communicated by either or both of the light sources 314.

The brightness of light source 314 may also be controllable, for example by changing the duty cycle of a pulse width modulated (PWM) driving circuit. In some embodiments, monitoring device 100 includes an ambient light sensor 317, and adjusts the brightness of light source 314. For example, during the day in a brightly lit room, light source 314 may be illuminated brightly, for good visibility. However, at night, in a dimly lit bedroom or darkened hospital ward, the full brightness of light source 314 may be distracting, while even a dim light may be readily visible. In that case, the brightness of light source 314 may be reduced accordingly, to reduce the distraction caused by light source 314.

In some embodiments, monitoring device 100 may include a sound generator 315, for signaling the patient. Sound generator 315 may be activated to notify the user of a condition that may compromise the operation of monitoring device 100 or for other uses. For example, a signal may be activated to notify the patient that electrical conductivity to the patient's skin has been lost, that wireless connectivity to intermediate device 403 has been lost, or that some other urgent condition exists. The nature of the condition may be indicated by one or more of the pitch, loudness, or beeping pattern of sound generator 315, or by some other aspect of the generated sound.

Due to variations in hearing ability between patients, some patients may be able to hear frequencies that other patients may not, and vice versa. In order to improve the chance that a particular patient will be able to hear sound generator 315, sound generator 315 may be controlled to produce sounds containing multiple or different frequencies. In one embodiment, sound generator 315 is driven at 850 Hz and then at 950 Hz. In other embodiments, multiple frequencies may be generated simultaneously.

In some embodiments, monitoring device 100 may include a humidity sensor 317, configured to detect the ingress of water into reusable portion 102. For example, humidity sensor 317 may be a resistive or capacitive humidity sensor. Humidity sensor 317 is preferably coupled to processor 307, which can monitor the output of humidity sensor 317 to detect a threshold level of moisture or a change in moisture inside reusable portion 102 that might indicate ingress of moisture into reusable portion 102. When moisture ingress is detected, processor may signal the user using light source 314 or sound generator 315, may transmit an indication of the detection to a remote server using wireless communication circuitry 310, or may take another action.

Preferably, before use of a particular monitoring device 100, the unique identifiers of disposable portion 101 and reusable portion 102 are recorded and matched in a database, to indicate that the two portions are authorized for use together. This pairing may be done before shipment of the device to a particular patient. As is explained in more detail below, reusable portion 102 may be used serially with a number of disposable portions 101. In this case, a pre-packaged set of one reusable portion 102 and a number of disposable portions 101 may be shipped together, and their unique identifiers may be recorded as a set in the database.

When disposable portion 101 and reusable portion 102 are assembled together, processor 307 may request the unique identifier of disposable portion 101. If no unique identifier is received, it may be assumed that a malfunction has occurred, or that the disposable portion may be counterfeit and not trustworthy, or that some other circumstance has occurred that may prevent reliable monitoring. If no identifier is received from disposable portion 101, processor 307 may simply refuse to proceed with monitoring.

In other embodiments, reusable portion 102 may be loaded at the time of shipment with the unique identifiers of all disposable portions 101 with which reusable portion 102 is intended to be used. On power up, reusable portion 102 may read the unique identifier of the particular disposable portion 101 into which it has been assembled, and compare the identifier with its stored list of acceptable identifiers. If the identifier is not found, reusable portion 102 may simply not initiate monitoring. If the identifier is found in the list, then monitoring begins as normal.

Figure 4:
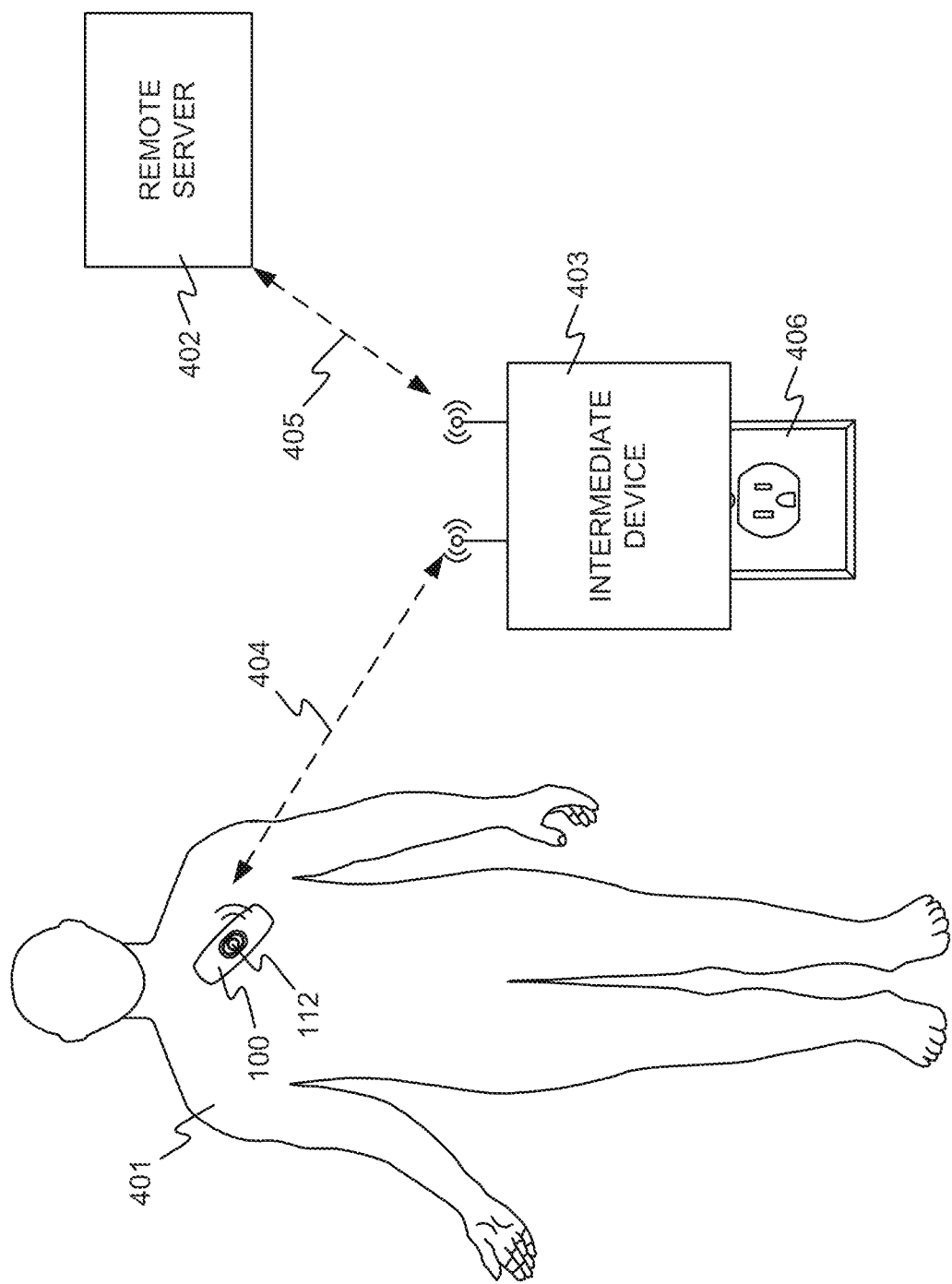
FIG. 4 illustrates the monitoring device of FIGS. 1A and 1B adhered to a patient.

In other embodiments, reusable portion 102 may retrieves unique identifier 303 of disposable portion 101 and report it, along with the unique identifier of reusable portion 102, to remote server 402 for determination whether the two portions are intended to be used together. If records indicate that the two portions are not intended for use together, remote server 402 may alert monitoring personnel. Even when a mismatch is detected, monitoring device 100 may commence monitoring, including the storing of sampled data and the transmission of event reports, and remote server 402 may accept the transmitted data. However, the fact that an unexpected disposable portion 101 is detected may indicate the possibility of product misuse or unreliable monitoring, which can then be investigated Assuming that monitoring is to proceed, monitoring device 100 is adhered to a patient 401, for example as shown in FIG. 4. In some uses, disposable portion 101 may be adhered to patient 401 and then reusable portion 102 assembled into it, and in other uses, monitoring device 100 may be assembled before being adhered to patient 401.

Under control of processor 307, monitoring device 100 may monitor one or more different physiological parameters of patient 401. For example, an electrocardiogram (ECG) of patient 401 may be recorded from signals sampled from two or more of electrodes 103a-103d. In some embodiments, the ECG is taken by sampling the voltage between two of electrodes 103a-103d with a frequency rapid enough to detect the subtle electrical signals produced by the heart of patient 401. For example, the voltage may be sampled with a frequency of 50-1000 Hz. In one embodiment, the voltage is sampled with a frequency of 200 Hz (once every 5 milliseconds). The voltage may be sampled using an analog-to-digital converter (ADC), for example an ADC built into or connected to processor 307.

The circuitry used to sense signals from electrodes 103a-103d may be collectively referred to as sensing circuitry. For example, sensing circuitry may include signal conditioning circuitry 308 and processor 307, as well as various amplifiers, ADCs, and the like. Many different arrangements are possible.

In some embodiments, the ECG data may be filtered to remove the effects of interference from common noise sources such as the mains power line. For example, a raw ECG signal may be sampled at a higher frequency than its ultimate recorded sampling frequency, and digitally filtered. In one embodiment, the raw ECG sampling is done at 600 Hz, the raw data are digitally filtered to remove 50 Hz or 60 Hz power line noise, and the data are downsampled to 200 Hz for recording.

More information about the recording of an ECG may be found in U.S. Patent Application Publication No. 2013/0274584 published Oct. 17, 2013 and titled "Heuristic Management of Physiological Data", the entire disclosure of which is incorporated by reference herein for all purposes.

In some embodiments, the sampled data (e.g. the 200 Hz ECG voltage samples) are stored in a non-volatile portion of memory 309. Depending on the resolution of the ADC, each sample may require 8-16 bits of storage, such that 180 hours of sampled data can be conveniently stored in available memory sizes. For the purposes of this disclosure, this stored information may be referred to as "complete" data.

All monitored information may be encrypted and stored in memory 309, such that the data can be decrypted only using a key or keys. Encryption may be performed using an algorithm such as RSA, DSS, or another kind of algorithm. Thus, should reusable portion 102 be lost after monitoring the condition of a particular patient, it will not be possible for an unauthorized party to reconstruct sensitive medical information about the patient. In addition, any transmissions of data may also be encrypted.

Another example of a physiological parameter that may be monitored by monitoring device 100 is the patient's tissue hydration level. Increased fluid retention in the tissues of the body is a symptom of acute cardiac decompensation heart failure, and may be reflected in the electrical impedance of the patient's tissue. Tissue impedance may be measured, for example, by forcing a known electrical current through outer electrodes 103b and 103c, and measuring the voltage impressed between electrodes 103a and 103d. The current may be alternating current, at an excitation frequency selected to most effectively characterize the tissue hydration. More information about tissue hydration measurement may be found in U.S. Patent Application Publication No. 2009/0076345 previously incorporated by reference, and U.S. Patent Application Publication No. 2009/

0076344 published Mar. 19, 2009 and titled "Multi-Sensor Patient monitor to Detect Impending Cardiac Decompensation", the entire disclosure of which is incorporated by reference herein for all purposes.

Because tissue impedance is a slowly-changing parameter, impedance data need not be sampled as often as ECG data. For example, tissue impedance data samples may be taken and stored at a sampling frequency of 0.1 to 10 Hz (one sample every 0.1 to 10 seconds), or at another suitable frequency. Note that this sampling frequency is independent of the excitation frequency of the AC current used in taking the impedance measurements.

Still another example of a physiological parameter that may be monitored using monitoring device 100 is the patient's respiration. For example, the patient's breathing rate, breath volume, or other breathing characteristics may be monitored. Such breathing parameters may also be relevant in the diagnosis or prediction of acute decompensated heart failure. For example, a trend toward an increased breathing rate combined with reduced breath volume, so-called "shallow" breathing may be suggestive of impending heart failure.

The patient's breathing rate and volume may also be inferable from tissue impedance measurements, as the tissue impedance observed by monitoring device 100 may vary by a measurable amount as the patient inhales and exhales. (These variations are preferably filtered out when characterizing the impedance itself.) Impedance variations occurring in the frequency range of normal breathing may be analyzed to characterize the patient's breathing. More information about the relationship of impedance and respiration may be found in U.S. Patent Application Publication No. 2011/0245711, published Oct. 6, 2011 and titled "Method and Apparatus for Personalized Physiologic Parameters", the entire disclosure of which is incorporated by reference herein for all purposes.

Impedance samples for characterizing respiration may be taken and stored with a sampling frequency of 2 to 10 Hz, or another suitable sampling frequency. In one embodiment, data samples for measuring respiration are taken and stored with a sampling frequency of 4 Hz.

Other examples of physiological parameters that may be monitored using monitoring device 100 are aspects of the patient's orientation, activity, or other parameters that may be measured using accelerometer 313. For example, signals produced by accelerometer 313 may be used to determine if the patient is lying down or is upright. In addition, the signals may be used to determine the patient's activity level, for example whether the patient is sedentary, exercising, or the like. In some cases, the intensity or type of exercise may be ascertainable from the accelerometer signals. Certain abrupt accelerometer signals may indicate that the patient has fallen.

Accelerometer signals may be taken and stored with a sampling frequency of 0.1 to 10 Hz, or another suitable sampling frequency. In one embodiment, data samples from accelerometer 313 are taken and stored with a sampling frequency of 0.25 Hz, or one sample every 4 seconds.

In addition to storing sampled data from the various sensors on monitoring device 100, processor 307 may continually monitor and analyze the sampled data to detect physiological events of patient 401. For example, the ECG samples may be compared with templates characterizing different possible arrhythmias, and the occurrence of an arrhythmia may be considered an event. In another example, ongoing impedance measurements may indicate that the patient's tissue hydration has elevated above a predetermined threshold value, as compared with a baseline value measured at the beginning of the monitoring period. Because of the significance of tissue hydration in acute decompensated heart failure, this rise in tissue hydration may be considered a significant physiological event. In another example, an accelerometer reading that indicates that the patient has fallen may be considered a physiological event.

Event recognitions may also be derived from combinations of sensor data. For example, a rise in tissue hydration combined with a reduction in breath volume as compared with baseline values may be considered a physiological event. In another example, an increase in heart rate as indicated by the ECG data that is not accompanied by a commensurate increase in physical activity as indicated by signals from accelerometer 313 may be considered a physiological event. Many other event definitions are possible.

Example monitoring device 100 can report some or all detected events as the events occur, via wireless communication circuitry 310. When a particular arrhythmia is detected, monitoring device 100 may transmit a report of the physiological event via wireless communication circuitry 310 to an external device.

Referring again to FIG. 4, monitoring device 100 may report event indications to a remote server 402 via an intermediate device 403. For the purposes of this disclosure, either remote server 402 or intermediate device 403 may be considered an "external device" with which monitoring device 100 communicates.

Intermediate device 403 may communicate with monitoring device 100 wirelessly via link 404, which may be a short-range wireless link such as a Bluetooth®, ZigBee®, Wi-Fi® or other kind of standard or proprietary wireless link. In turn, intermediate device 403 communicates with remote server 402 using communication link 405, which may be a wide-area wireless connection such as a cellular telephone connection, or may be a wired connection. This arrangement enables patient 401 to go about his or her daily activities while monitoring is ongoing and events are reported. Remote server 402 may be, for example, at a monitoring facility, health care facility, or any other location worldwide where link 405 can be made. In other uses, remote server 402 may be adjacent patient. In some embodiments, no intermediate device may be necessary, and monitoring device 100 may communicate directly with a server that receives event reports.

In FIG. 4, intermediate device 403 is depicted as being connected to mains power outlet 406. For example, patient 401 may plug in intermediate device 403 at the patient's home or office. In other embodiments, intermediate device may also or alternatively be battery powered, enabling further flexibility on the part of patient. For example, patient 401 may carry a battery powered intermediate device 403 while going about daily errands. So long as link 405 is maintained, for example so long as patient 401 remains in an area with cellular telephone coverage, event reports can be transmitted promptly to remote server 402.

An event report may indicate that an event has been detected, may describe the event, and may also include a portion ("snippet") of the sampled data that prompted the event report. For example, if analysis of a portion of the sampled ECG determines that a particular arrhythmia has occurred, the event report may simply indicate that the arrhythmia was detected at a certain time. However, in some embodiments, report may also include sampled ECG data showing the arrhythmia occurring. A physician or other health care professional may use the transmitted data to verify that the event actually occurred, to evaluate the severity of the event, or for other purposes.

Even if events are not detected, monitoring device 100 may periodically report to remote server. For example, during ECG monitoring, monitoring device 100 may send an ECG data snippet after a predetermined time has elapsed without any event detections. The predetermined time may be any suitable interval, for example one hour, two hours, four hours, or another interval.

Patient 401 may also be able to trigger the sending of a data snippet using button 112. Considered another way, a press of button 112 may be considered an event, to which monitoring device 100 reacts by transmitting a data snippet. For example, if patient 401 experiences a symptom that he or she suspects may be related to the condition for which he or she is being monitored, patient 401 can press button 112, to cause monitoring device 100 to send data encompassing the time just before the button press to remote server 402 and preferably a period of time after the button press. For example, upon a press of button 112, monitoring device 100 may record an additional 30 seconds of data, and then transmit to server 402 45 seconds of data, including the 15 seconds before and the 30 seconds after the press of button 112. Of course, other intervals may be used, and the time period before the button press for which data is transmitted need not be the same as the time period after the button press for which data is transmitted. Examples of symptoms that may prompt a patient to press button 112 may include dizziness, syncope, chest pain, shortness of breath, or other symptoms.

Button 112 may activate a simple mechanical switch that makes or breaks electrical contacts as shown in FIG. 3, or may be another kind of input device. For example, button 112 may be implemented with a magnetic detector such as a Hall effect sensor coupled to processor 307, and the user may signal monitoring device 100 to capture and send a snippet of data by placing a magnet near reusable portion 102. In some embodiments, monitoring device 307 may preferably provide feedback to the user regarding the request to transmit a data snippet. For example, monitoring device may flash light source 314 or generate a sound using sound generator 315 to signal the user. Monitoring device 100 may signal the user of such events as that the button press or other request signal was received, that the data snippet was collected and sent, or other aspects of snippet collection and transmission.

In some embodiments, communication between remote server 402 and monitoring device 100 may be bidirectional. This capability may be used for a variety of purposes. For example, remote server 402 may download software updates to monitoring device 100, for upgrading the capabilities of monitoring device 100, for configuring monitoring device 100 to perform a different kind of monitoring than it has been performing, or for other purposes. In one example scenario, a data snippet transmitted as a result of a press of button 112 by patient 401 may prompt a reviewing physician to suspect a medical condition that had previously not been suspected for patient 401. In that case, remote server may send commands to monitoring device 100 reconfiguring it to add monitoring additional physiological parameters.

In another use of bidirectional communication, remote server may request snippets of sampled data "on demand" by sending requests to monitoring device 100. For example, a physician reviewing an event report sent by monitoring device 100 may wish to see more ECG data than was sent by monitoring device with the event report, or may wish to see data from a different kind of sensor present on monitoring device. In an example scenario, patient 401 may feel dizzy and press button 112, prompting monitoring device 100 to send a snippet of ECG data to remote server 402. If a review of the data snippet does not reveal any abnormality that might explain the patient's symptoms, a reviewing physician may request that respiration and activity data from just before the time of the button press also be transmitted, in case the additional data might assist in determining the cause of the patient's symptoms.

In some embodiments, monitoring device 100 or remote server 402 may monitor the quality of the electrode contact with the patient's skin. For example, if monitoring device 100 or remote server 402 receives a tissue impedance reading that is higher than normal bounds for human tissue, the reading may be flagged as possibly indicating a loss of contact between the patient's skin and one or more of electrodes 103a-103d. Any of various actions may be taken upon the suspected detection of a loss of electrode contact. For example, monitoring device 100 may use light source 314 or sound generator 315 to signal a potential problem to the patient, using a light pattern, light color, or sound that signals the user to contact a help line for instructions about responding to the problem. In another scenario, remote server 402 may flag the potential loss of contact, and a customer service representative may call the patient directly to ask what may have precipitated the suspect reading or readings. If electrode contact has been lost, the patient may be directed to visit a clinic of other medical facility for replacement of disposable portion 101. In some embodiments, a single suspect impedance reading may not trigger intervention, but action may be taken if the elevated impedance persists for a predetermined period, for example a few minutes to a few hours.

In some embodiments, monitoring device 100 can be used for extended monitoring through the use of multiple disposable portions 101 with a single reusable portion 102. For example, each disposable portion 101 may have a usable life shorter than the period for which monitoring is desired. In some embodiments, each disposable portion 101 can be used for over one week or more, for example 180 hours or more, without replacement. The useful life of disposable portion 101 may be limited by the capacity of battery 301, the ability of the adhesive holding the device to the patient's skin to maintain good electrical contact between electrodes 103a-103d and the patient's skin, and other factors.

When a disposable portion 101 has reached the end of its useful life, the patient preferably returns to a clinic or other medical facility for replacement of disposable portion 101. Monitoring device 100 is removed from the patient's skin, and reusable portion 102 is separated from disposable portion 101. In some embodiments, the separation of disposable and reusable portions 101 and 102 renders disposable portion 101 unusable. For example, the act of removing reusable portion 102 may damage electrical traces within disposable portion 101, may damage the mechanical features that hold the two portions together, or may cause other damage to disposable portion 101. Rendering disposable portion 101 unusable discourages attempted reuse of disposable portion 101, which could result in unreliable monitoring.

If a reused disposable portion 101 were to be assembled with a particular reusable portion 102, the attempted reuse may be detected. For example, if the reused disposable portion 101 has not been paired with the particular reusable portion 102, the reusable portion 102 may refuse to operate or may report the mismatch. Or data transfers from monitoring device 100 may include the unique identifiers of disposable portion 101 and reusable portion 102, and remote server 402 may detect the reuse when data is received bearing a disposable portion identifier for which data already exists from a prior monitoring session.

During the replacement process, the sampled data stored in reusable portion 102 may be read through connector 312. For example, a suitable cable may be attached between connector 312 and a computer system or other reader, and the data transferred to the reading device. In other embodiments, reusable portion 102 may be placed in a reading device configured to make contact with connector 312 on reusable portion 102. The reading device may be connected to a computer system that ultimately receives the data. Preferably, the retrieved data is associated with any event reports and data snippets received during monitoring of patient 401.

As will be appreciated, monitoring device 100 may thus make efficient use of resources, while communicating potentially urgent information in real time. The ongoing analysis of the sampled data and real time reporting of physiological events ensures that potentially urgent or significant events can be reviewed nearly as they occur. Thus, it may be unnecessary to transmit the entire set of sampled data wirelessly. In any event, transmitting the entire sampled data set wirelessly may be expensive or impracticable. However, the data may be useful for further analysis of the patient's condition, and it is therefore valuable for the data to be preserved and stored. Since urgent situations can be addressed with event reports and possible "on demand" retrieval of additional sampled data, it may not be urgent for the complete data to reach server 402 or another storage site. Transferring the complete data via cable or other wired connection during an office visit may complete the transfer quickly and at low cost.

Reusable portion 102 can then be assembled into a new disposable portion 101, and the resulting monitoring device 100 can be re-adhered to the patient's skin. Upon each reassembly, reusable portion 102 retrieves the unique identifier 303 of the new disposable portion 101 and a check is made, for example by reusable portion 102 or remote server 402. Monitoring can then continue for another period, up to the useful life of the new disposable portion 101. Many changes of disposable portion 101 may be performed, so that a patient may be monitored for up to 90 days or more.

Once monitoring of a patient is completed, reusable portion 102 may be cleaned, for example disinfected, so that it can be reused with a different patient. The architecture of monitoring device 100 may enable reusable portion 102 to be sealed from the external environment, and therefore able to withstand many cleaning and disinfection cycles so that reusable portion 102 can have an extended useful life. For example, because secondary battery 304 inside reusable portion 102 is re-charged from primary 301 in disposable portion 101, there is no need to open reusable portion 102 to change secondary battery 304. Also, since reusable portion 102 communicates wirelessly, the number of penetrations of the shell of reusable portion 102 is minimized.

In addition, the materials of the shell of reusable portion 102 may be selected to be compatible with one or more disinfectant solutions. Similarly, any adhesives used in the assembly of reusable portion 102 may be selected to be compatible with the disinfectant of choice. In some embodiments, a disinfectant and disinfection process may be selected in cooperation with the materials of reusable portion 102, to ensure compatibility.

Figure 5:
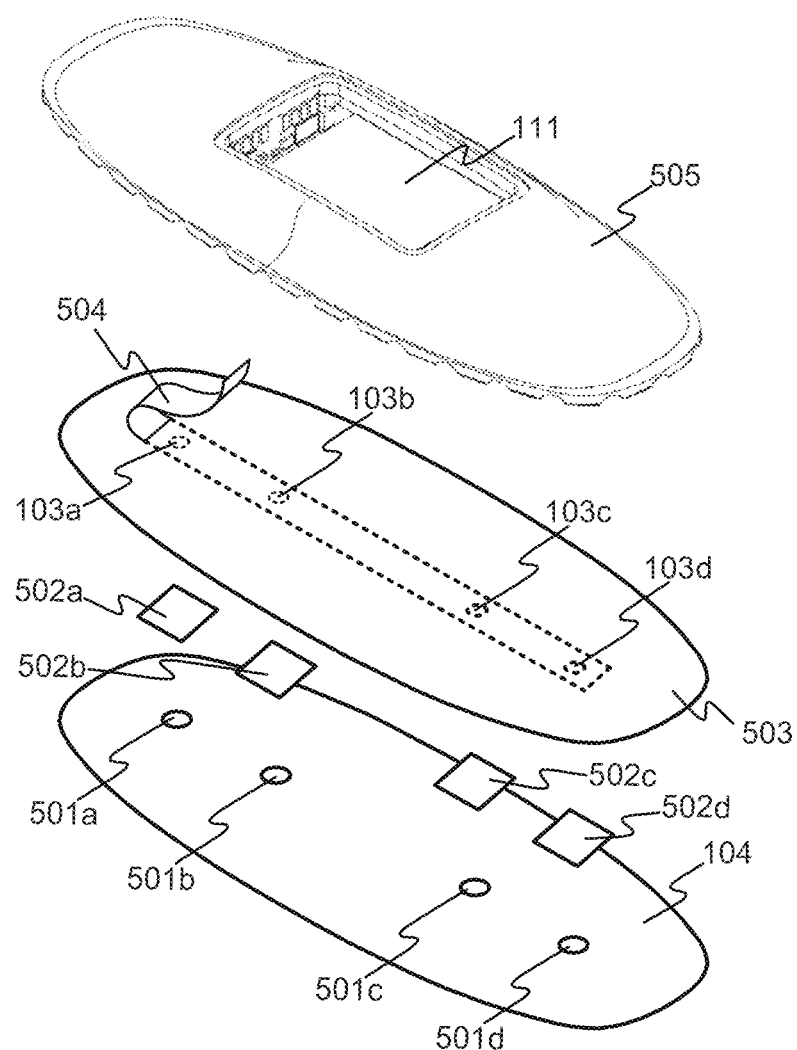
FIG. 5 illustrates the construction of an embodiment of a disposable portion in more detail.

FIG. 5 illustrates an exploded view of the construction of an embodiment of disposable portion 101 in more detail. Bottom layer 104, previously described, includes an adhesive on its underside (not visible in FIG. 5). Bottom layer 104 includes openings 501a-501d over which gels 502a-502d are positioned. Gels 502a-502d may be made, for example, of hydrogel adhesive 9880 available from the 3M Company of St. Paul, Minn., USA, or another suitable material.

An overlayer 503 is laminated to the top side of bottom layer 104, constraining gels 502a-502d and a flex circuit 504 between overlayer 503 and bottom layer 104. Overlayer 503 is also breathable, having a high moisture vapor transmission rate, for example at least 100 $g/m^2/24$ hrs, at least 400 $g/m^2/24$ hrs, or another suitable value. Flex circuit 504 includes electrodes 103a-103d. Finally, foam cover 505 bonds to the upper surface of overlayer 503, and defines an opening for pocket 111. The interior of pocket 111 is preferably defined by a molded part held by foam cover 505. Openings 506 remain open to the interior space formed between overlayer 503 and foam cover 505.

Figure 6:
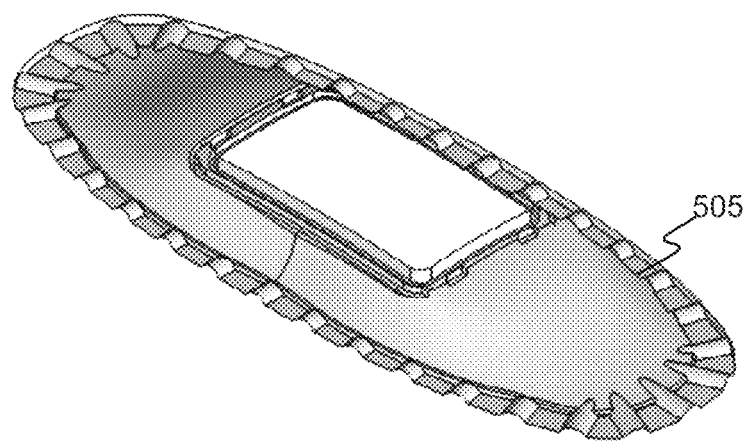
FIG. 6 illustrates an underside view of a foam cover, in accordance with embodiments.

FIG. 6 illustrates an underside view of foam cover 505, in accordance with embodiments.

Figure 7:
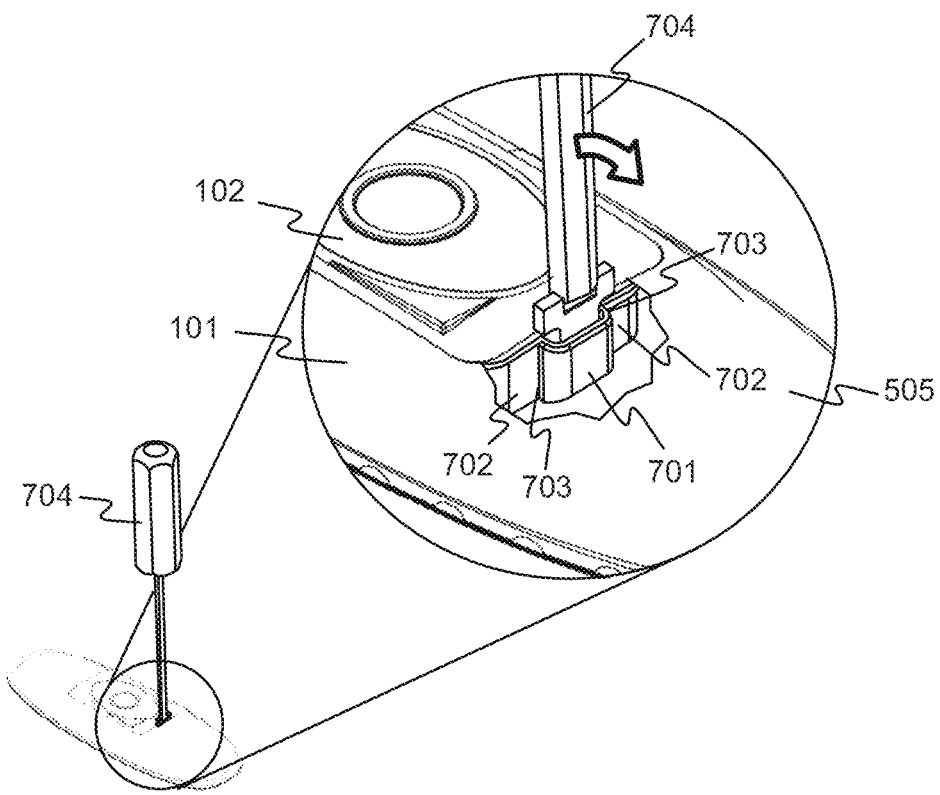
FIG. 7 illustrates a technique for rendering the disposable portion of the device of FIGS. 1A and 1B unusable, according to embodiments.

FIG. 7 illustrates a technique for rendering disposable portion 101 unusable when reusable portion 102 is removed, according to embodiments. In particular, FIG. 7 provides a magnified cutaway illustrating the removal of disposable portion 101 from reusable portion 102 using tool 704. As illustrated in the magnified cutaway portion, disposable portion 101 is configured to receive and retain reusable portion 102. In particular, disposable portion 101 includes recess 701, a ledge portion (not visible in this view) that engages snap feature 201 of reusable portion 102, and enclosure walls 702 that intersect with recess 701 at corners 703.

In one embodiment shown in FIG. 7, wall 702 is weaker than the walls of recess 701 or include thin or otherwise weakened areas. As a result, insertion of tool 704 through foam cover 505 and into recess 701 and application of force in the direction indicated by the arrow (i.e., downward rotating about the end of tool 704), results in recess 701 being pried away from wall 702 and eventual breaking of a portion of wall 702. As a result of the dislocation of wall 702, the ledge is similarly displaced, such that snap feature 201 (shown in FIG. 2A) is no longer held in place by the ledge. The dislocation of the ledge is illustrated in additional detail in both the unbroken and broken states In the process, the ledge for engaging snap feature 201 is displaced and no longer in position to hold reusable portion 102 in disposable portion 101.

Figure 8A:
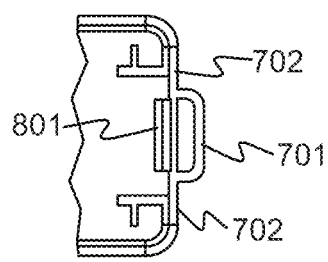
FIGS. 8A and 8B show additional details of the technique of FIG. 7.
Figure 8B:
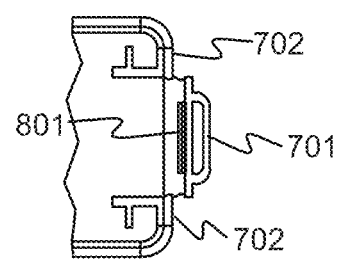

FIGS. 8A and 8B show top views of recess 701 and the breakage of wall 702, resulting in the displacement of ledge 801. In particular, FIG. 8A illustrates wall 702 in an unbroken state. As a result, ledge 801 is positioned to engage with snap feature 201 (not shown in this view). Recess 701 is clearly shown, including a portion of recess 701 configured to receive tool 704. FIG. 8B illustrates wall 702 in a broken state, as a result of tool 704 being placed into recess 701, and rotated in a downward (in this view, to the right) direction until the applied force causes wall 702 to break. As a result of wall 702 breaking, ledge 801 is displaced at an angle downward and to the right, such that ledge 801 no longer engages snap feature 201. As a result, reusable portion 102 can be removed from disposable portion 101, and disposable portion 101 is discarded. A benefit of this embodiment is disposable portion 101 can no longer be used to retain reusable portion 101, and therefore must be discarded as desired.

According to one embodiment of the present invention, a monitoring device for monitoring one or more physiological parameters of a patient includes a disposable portion and a reusable portion. The disposable portion comprises at least two electrodes for coupling to the skin of the patient, a primary battery, and a first set of electrical contacts. The reusable portion comprises a processor, memory, a second set of electrical contacts, and sensing circuitry coupled to the at least two electrodes, wherein the reusable portion is mechanically coupleable to the disposable portion and wherein the reusable portion is electrically coupleable to the disposable portion through the first and second electrical contacts. When the reusable portion and the disposable portion are electrically coupled through the first and second electrical contacts, signals from the at least two electrodes are passed to the sensing circuitry and processed by the processor, and wherein the sensing circuitry and the processor are powered from the primary battery through the coupled first and second electrical contacts. When the reusable portion and the disposable portion are mechanically uncoupled after having been mechanically coupled, the disposable portion is rendered unusable by the process of mechanically uncoupling the reusable portion and the disposable portion.

The monitoring device of the preceding paragraph may optionally include, additionally and/or alternatively, one or more of the following features, configurations and/or additional components.

The reusable portion and the disposable portion may be separable, wherein the reusable portion may be used with a different disposable portion.

In any of the preceding embodiments, the reusable portion may comprise a real time clock and a secondary battery that powers the real time clock, and wherein when the reusable portion and the disposable portion are coupled through the first and second electrical contacts, the secondary battery is charged from the primary battery through the first and second electrical contacts.

In any of the preceding embodiments, the monitoring device may further comprise wireless communication circuitry through which information can be transmitted to an external device.

In any of the preceding embodiments, the processor may be programmed to: analyze data sampled from the signals from the electrodes; based on the analysis of the signals form the electrodes, identify a physiological event of the patient; and transmit a report of the physiological event via the wireless communication circuitry to the external device.

In any of the preceding embodiments, the processor may be configured to continuously record data sampled from the signals from the electrodes in the memory during monitoring.

In any of the preceding embodiments, the monitoring device may store the data in an encrypted form.

In any of the preceding embodiments, the processor may be configured to continuously transmit recorded data to an external device.

In any of the preceding embodiments, the monitoring device may further comprise a data interface comprising a connector, and wherein the continuously recorded data may be transmitted to the external device via a wired connection through the connector.

In any of the preceding embodiments, the processor may be configured to, during monitoring: receive, from an external device via the wireless communication circuitry, a request to transmit a portion of the continuously recorded data to the external device; and transmit the requested portion of the continuously recorded data to the external device via the wireless communication circuitry.

In any of the preceding embodiments, the one or more physiological parameters monitored by the monitoring device may include an electrocardiogram of the patient.

In any of the preceding embodiments, the one or more physiological parameters monitored by the monitoring device may include a tissue impedance the patient.

In any of the preceding embodiments, the one or more physiological parameters monitored may include a tissue hydration of the patent, and wherein the tissue hydration is derived from the tissue impedance the patient.

In any of the preceding embodiments, the one or more physiological parameters monitored may include any two or more of the parameters selected from the group consisting of an electrocardiogram of the patient, a tissue impedance the patient, a tissue hydration of the patient, and an activity level of the patient.

In any of the preceding embodiments, the disposable portion may be rendered unusable by breaking a mechanical feature of the disposable portion.

In any of the preceding embodiments, the reusable portion may include a unique reusable portion identifier stored in the reusable portion and accessible to the processor; and the disposable portion includes a unique disposable portion identifier stored in the disposable portion and accessible to the processor In any of the preceding embodiments, the reusable portion may be capable of withstanding multiple cleaning and disinfection cycles without compromising the usability of the device In any of the preceding embodiments, when the reusable portion and the disposable portion are coupled together, the device may be capable of withstanding being splashed with water without compromising the usability of the device In any of the preceding embodiments, the processor may be initially programmed such that the device is configured to monitor a particular set of one or more physiological parameters, and wherein the processor can be reprogrammed such that the device is configured to monitor a different set of one or more physiological parameters.

According to another embodiment of the present invention, a monitoring device for monitoring one or more physiological parameters of a patient includes a disposable portion and a reusable portion. The disposable portion includes at least two electrodes for coupling to the skin of the patient, and a first set of electrical contacts. The reusable portion includes a processor, memory, a second set of electrical contacts, and sensing circuitry coupled to the at least two electrodes, wherein the reusable portion is mechanically coupleable to the disposable portion and wherein the reusable portion is electrically coupleable to the disposable portion through the first and second electrical contacts. When the reusable portion and the disposable portion are electrically coupled through the first and second electrical contacts, signals from the at least two electrodes are passed to the sensing circuitry and processed by the processor. In addition, the reusable portion includes a unique reusable portion identifier stored in the reusable portion and accessible to the processor, and the disposable portion includes a unique disposable portion identifier stored in the disposable portion and accessible to the processor.

According to another embodiment of the present invention, a monitoring device for monitoring one or more physiological parameters of a patient includes a disposable portion and a reusable portion. The disposable portion includes at least two electrodes for coupling to the skin of the patient, and a first set of electrical contacts. The reusable portion includes a processor, memory, a second set of electrical contacts, sensing circuitry coupled to the at least two electrodes, wireless communication circuitry through which information can be transmitted to an external device, and a data interface comprising a connector for transmitting data via wired connection using the connector. The reusable portion is mechanically coupleable to the disposable portion and wherein the reusable portion is electrically coupleable to the disposable portion through the first and second electrical contacts. When the reusable portion and the disposable portion are electrically coupled through the first and second electrical contacts, signals from the at least two electrodes are passed to the sensing circuitry and processed by the processor.

According to another embodiment of the present invention, a monitoring device for monitoring one or more physiological parameters of a patient includes a disposable portion and a reusable portion. The disposable portion includes at least two electrodes for coupling to the skin of the patient, a primary battery, and a first set of electrical contacts. The reusable portion comprising a processor, memory, a second set of electrical contacts, a secondary battery, a real time clock powered by the secondary battery, and sensing circuitry coupled to the at least two electrodes. The reusable portion is mechanically coupleable to the disposable portion and wherein the reusable portion is electrically coupleable to the disposable portion through the first and second electrical contacts. When the reusable portion and the disposable portion are electrically coupled through the first and second electrical contacts, signals from the at least two electrodes are passed to the sensing circuitry and processed by the processor. The sensing circuitry and the processor are powered from the primary battery through the coupled first and second electrical contacts. When the reusable portion and the disposable portion are coupled through the first and second electrical contacts, the secondary battery is charged from the primary battery through the first and second electrical contacts.

According to another embodiment of the present invention, a monitoring device for monitoring one or more physiological parameters of a patient includes a disposable portion and a reusable portion. The disposable portion includes at least two electrodes for coupling to the skin of the patient, a battery, and a first set of electrical contacts. The reusable portion includes a processor, memory, a second set of electrical contacts, and sensing circuitry coupled to the at least two electrodes. The reusable portion is mechanically coupleable to the disposable portion such that when the reusable portion and the disposable portion are mechanically coupled they form a water-resistant unit, and wherein the reusable portion is electrically coupleable to the disposable portion through the first and second electrical contacts. When the reusable portion and the disposable portion are electrically coupled through the first and second electrical contacts, signals from the at least two electrodes are passed to the sensing circuitry and processed by the processor. The sensing circuitry and the processor are powered from the battery through the coupled first and second electrical contacts. The reusable portion and the disposable portion are separable, and wherein the reusable portion can be used with a different disposable portion.

The monitoring device of the preceding paragraph may optionally include, additionally and/or alternatively, one or more of the following features any of the preceding embodiments.

For example, the battery may be a primary battery.

In any of the preceding embodiments, the reusable portion may include a real time clock and a secondary battery that powers the real time clock, and wherein when the reusable portion and the disposable portion are coupled through the first and second electrical contacts, the secondary battery is charged from the primary battery through the first and second electrical contacts.

In any of the preceding embodiments, the reusable portion may further include wireless communication circuitry through which information can be transmitted to an external device.

In any of the preceding embodiments, the processor may be programmed to: analyze data sampled from the signals from the electrodes; based on the analysis of the signals form the electrodes, identify a physiological event of the patient; and transmit a report of the physiological event via the wireless communication circuitry to the external device.

In any of the preceding embodiments, the processor may be configured to cause data sampled from the signals from the electrodes to be continuously recorded in the memory during monitoring.

In any of the preceding embodiments, the data may be stored in an encrypted form.

In any of the preceding embodiments, the processor may be configured to transmit the continuously recorded data to an external device.

In any of the preceding embodiments, the monitoring device may further include a data interface that includes a connector, and wherein the continuously recorded data is transmitted to the external device via a wired connection through the connector.

In any of the preceding embodiments, the processor may be configured to, during monitoring: receive, from an external device via the wireless communication circuitry, a request to transmit a portion of the continuously recorded data to the external device; and transmit the requested portion of the continuously recorded data to the external device via the wireless communication circuitry.

In any of the preceding embodiments, the one or more physiological parameters monitored may include an electrocardiogram of the patient.

In any of the preceding embodiments, the one or more physiological parameters monitored may include a tissue impedance the patient.

In any of the preceding embodiments, the one or more physiological parameters monitored may include a tissue hydration of the patent, and wherein the tissue hydration is derived from the tissue impedance the patient.

In any of the preceding embodiments, the one or more physiological parameters monitored may include any two or more of the parameters selected from the group consisting of an electrocardiogram of the patient, a tissue impedance the patient, a tissue hydration of the patient, and an activity level of the patient.

In any of the preceding embodiments, the disposable portion may be rendered unusable by breaking a mechanical feature of the disposable portion.

In any of the preceding embodiments, the reusable portion may further include a unique reusable portion identifier stored in the reusable portion and accessible to the processor; and the disposable portion includes a unique disposable portion identifier stored in the disposable portion and accessible to the processor.

In any of the preceding embodiments, the reusable portion may be capable of withstanding multiple cleaning and disinfection cycles without compromising the usability of the device.

In any of the preceding embodiments, when the reusable portion and the disposable portion are coupled together, the device may be able to withstand being splashed with water without compromising the usability of the device.

In any of the preceding embodiments, the processor may be initially programmed such that the device is configured to monitor a particular set of one or more physiological parameters, and wherein the processor may be reprogrammed such that the device is configured to monitor a different set of one or more physiological parameters.

According to another embodiment of the present invention, A monitoring device for monitoring an electrocardiogram of the patient may include a disposable portion and a reusable portion. The disposable portion may include a shell having a bay and a first surface for adhering to the skin of a patient. The disposable portion may include at least two skin electrodes on the first surface of the shell, a battery housed within the shell, and a first set of electrical contacts within the bay and in electrical communication with the battery and the skin electrodes. The reusable portion may be releasably received and mechanically coupled within the bay of the disposable portion, the reusable portion comprising a monitoring circuit and a second set of electrical contacts in electrical communication with the monitoring circuit; the bay of the disposable portion and the reusable portion including interlocking features that releasably lock the reusable portion in the bay of the disposable portion with the second set of electrical contacts in electrical contact with the first set of electrical contacts such that the skin electrodes and battery of the disposable portion are in electrical communication with the monitoring circuit of the reusable portion.

In any of the preceding embodiments, the shell of the disposable portion may have a second surface and a frame extending into the shell from the second surface to define the bay, the first and second surfaces being formed of one or more flexible, breathable materials, the frame and reusable portion being rigid relative to the first and second surfaces of the disposable portion such that the monitoring device is adapted to conform to the skin of a patient.

In any of the preceding embodiments, the bay may include first and second ends, the first set of electrical contacts being arranged along the first end, the interlocking features including a breakable feature arranged along the second end.

In any of the preceding embodiments, the first surface of the disposable portion may be formed of material having a high moisture vapor transmission rate.

In any of the preceding embodiments, the first surface of the disposable portion may be formed of material having a moisture vapor transmission rate of at least 100 g/m$^2$/24 hrs.

In any of the preceding embodiments, the moisture vapor transmission rate may be at least 400 g/m$^2$/24 hrs.

In any of the preceding embodiments, the first surface of the disposable portion may include skin adhesive material for adhering the first surface to the skin of patient.

In any of the preceding embodiments, the reusable portion may include a sealed housing, and the first and second surfaces of the disposable portion are breathable.

In one embodiment, a method of using the monitoring device described in a previous embodiment may include removing the reusable portion from the disposable portion after a use of the monitoring device and replacing the disposable portion.

The invention has now been described in detail for the purposes of clarity and understanding. However, those skilled in the art will appreciate that certain changes and modifications may be practiced within the scope of the appended claims.

What is claimed is:

1. A monitoring device for monitoring one or more physiological parameters of a patient, the monitoring device comprising:

a disposable portion comprising at least two electrodes for coupling to a portion of skin of the patient, a battery, a first set of electrical contacts, a cover, a pocket for receiving a reusable portion, a ledge portion, and a recess; wherein the pocket is defined by a plurality of walls provided below a top surface of the cover, wherein the recess is configured adjacent to one of the plurality of walls and to receive an uncoupling tool, wherein the recess intersects with the adjacent wall at a first and second corner, and wherein the adjacent wall that intersects with the recess is structurally weaker than the walls associated with the recess; and the reusable portion comprising a snap feature, processor, memory, a second set of electrical contacts, and sensing circuitry coupled to the second set of electrical contacts, wherein the reusable portion is mechanically coupleable to the disposable portion, the plurality of walls surround the reusable portion, wherein the snap feature engages with the ledge portion to retain the reusable portion within the pocket, and wherein the reusable portion is electrically coupleable to the disposable portion through the first and second electrical contacts;

wherein when the reusable portion and the disposable portion are electrically coupled through the first and second electrical contacts, signals from the at least two electrodes are passed to the sensing circuitry and processed by the processor;

wherein the sensing circuitry and the processor are powered from the battery through the coupled first and second electrical contacts; and wherein the reusable portion and the disposable portion are configured to be mechanically uncoupled by applying force with the uncoupling tool after having been mechanically coupled, and the disposable portion is configured to be rendered unusable by the force causing the wall adjacent to the recess to break and the ledge to be displaced to where the ledge is no longer in position to hold the reusable portion in the disposable portion.

2. The monitoring device of claim 1, wherein the battery is a primary battery.

3. The monitoring device of claim 2, wherein the reusable portion comprises a real time clock and a secondary battery that powers the real time clock, and wherein when the reusable portion and the disposable portion are coupled through the first and second electrical contacts, the secondary battery is charged from the primary battery through the first and second electrical contacts.

4. The monitoring device of claim 1, wherein:
the reusable portion includes a unique reusable portion identifier stored in the reusable portion and accessible to the processor; and
the disposable portion includes a unique disposable portion identifier stored in the disposable portion and accessible to the processor.

5. The monitoring device of claim 1, wherein the reusable portion further includes wireless communication circuitry through which information can be transmitted to an external device, and a data interface comprising a connector for transmitting data via wired connection using the connector.

6. The monitoring device of claim 1, wherein the ledge is located adjacent to the recess.

7. The monitoring device of claim 6, wherein the ledge extends across a portion of the recess nearest to the pocket, and is affixed to the adjacent wall that intersects with the recess.

8. The monitoring device of claim 7, wherein the ledge extends into the pocket area to engage with the snap feature associated with the reusable portion.

9. The monitoring device of claim 6, wherein mechanically uncoupling the reusable portion from the disposable portion necessarily results in breaking the wall adjacent to the recess such that the snap feature is not engaged with the ledge portion and renders the disposable portion unusable.

10. The monitoring device of claim 1, wherein when the reusable portion is mechanically coupled within the disposable portion, the plurality of walls surround the reusable portion to form a water-resistant unit.

11. The monitoring device of claim 1, wherein the reusable portion includes a humidity sensor configured to detect an ingress of water into the reusable portion.

12. The monitoring device of claim 1, wherein the reusable portion can withstand multiple cleaning and disinfection cycles for reuse with a different patient without compromising the usability of the device.

13. A monitoring device for monitoring one or more physiological parameters of a patient, the monitoring device comprising:

a disposable portion comprising at least two electrodes for coupling to a portion of skin of the patient, a battery, a first set of electrical contacts, a cover, a pocket for receiving a reusable portion, a ledge portion, and a recess; wherein the pocket is defined by a plurality of walls provided below a top surface of the cover, wherein the recess is configured adjacent to one of the plurality of walls and to receive an uncoupling tool, wherein the recess intersects with the adjacent wall at a first and second corner; and wherein the adjacent wall that intersects with recess is structurally weaker than the walls associated with the recess; and the reusable portion comprising a snap feature, processor, memory, a second set of electrical contacts, and sensing circuitry coupled to the second set of electrical contacts, wherein the reusable portion is mechanically coupleable to the disposable portion, the plurality of walls surround the reusable portion, wherein the snap feature engages with the ledge portion to retain the reusable portion within the pocket, and wherein the reusable portion is electrically coupleable to the disposable portion through the first and second electrical contacts;

wherein when the reusable portion and the disposable portion are electrically coupled through the first and second electrical contacts, signals from the at least two electrodes are passed to the sensing circuitry and processed by the processor;

wherein the sensing circuitry and the processor are powered from the battery through the coupled first and second electrical contacts;

wherein the reusable portion and the disposable portion are configured to be mechanically uncoupled by applying force with the uncoupling tool after having been mechanically coupled, and the disposable portion is configured to be rendered unusable by the force causing the wall adjacent to the recess to break and the ledge to be displaced to where the ledge is no longer in position to hold the reusable portion in the disposable portion; and wherein the reusable portion comprises an outer surface, and wherein the disposable portion comprises an outer surface, and wherein the outer surface of the reusable portion and the outer surface of the disposable portion are sized, shaped, and arranged such that mechanically coupling the reusable portion to the disposable portion forms a contiguous outer surface of the monitoring device.

* * * * *